US00PP24635P3

(12) United States Plant Patent
Olesen

(10) Patent No.: US PP24,635 P3
(45) Date of Patent: Jul. 15, 2014

(54) COMPACT FLORIBUNDA ROSE PLANT NAMED 'POULPAL036'

(50) Latin Name: ***Rosa* hybrid**
Varietal Denomination: Poulpal036

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 91 days.

(21) Appl. No.: 13/507,027

(22) Filed: May 31, 2012

(65) Prior Publication Data

US 2013/0326765 P1 Dec. 5, 2013

(51) Int. Cl.
*A01H 5/00* (2006.01)

(52) U.S. Cl.
USPC ..... Plt./148; Plt./101; Plt./141

(58) Field of Classification Search
USPC ..... Plt./101, 141, 148
See application file for complete search history.

*Primary Examiner* — Susan McCormick Ewoldt

(57) ABSTRACT

A new garden rose plant of the Compact Floribunda class which has abundant, pink flowers and attractive foliage. This new and distinct variety has shown to be uniform and stable in the resulting generations from asexual propagation.

1 Drawing Sheet

Botanical designation: *Rosa* hybrid.
Variety denomination: 'Poulpal036'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2000 and the resulting seeds were planted in a controlled environment in Fredensborg, Denmark. The new variety, named 'Poulpal036', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal036' from all other varieties of which we are aware.

As part of the rose development program, Mogens N. Olesen germinated the seeds from the aforementioned hybridization during winter of 2000 and conducted evaluations on the resulting seedlings in a controlled environment in Fredensborg, Denmark. 'Poulpal036' was selected in the spring of 2001 by the inventor as a single plant from the progeny of the aforementioned hybridization.

Asexual reproduction of 'Poulpal036' by traditional budding and rooted cuttings was first done by Mogens N. Olesen in the nursery in Fredensborg, Denmark in July, 2001. This initial and other subsequent asexual propagations conducted in controlled environments have demonstrated that the characteristics of 'Poulpal036' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems on 2 year old plants of 'Poulpal036'. Specifically illustrated in the drawing are flowers at various stages of development, flower in parts, leaves, and stems.

DETAILED DESCRIPTION OF THE VARIETY

The following is a description of 'Poulpal036', as observed in its growth in in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poulthe', U.S. Plant Pat. No. 10,883 are compared to 'Poulpal036' in Chart 1.

CHART 1

| | 'Poulpal036' | 'Poulthe' |
|---|---|---|
| Petal Count | 65 | 55 to 60 |
| Flower Diameter | 80 to 90 mm | 40 to 50 mm |
| Petal Color After Opening, Upper Surface | Red-Purple Group 65A splashed with Red-Purple Group 62D at the base. | Red-Purple Group 57C |

FLOWER AND FLOWER BUD

Blooming habit: Continuous.
Flower bud:

*Size*.—Upon opening, 22 mm in length from base of receptacle to end of bud. Bud diameter is 18 mm.

*Bud form*.—Urceolate.

*Bud color*.—As sepals divide petals are Red-Purple Group 58C.

*Sepal inner surface*.—Color: Green Group 138C. Weak intonations of Greyed-Red Group 182A. Surface: Smooth with strong pubescence.

*Sepal outer surface*.—Color: Green Group 138B with strong intonations of Greyed-Purple Group 183A. Texture: Somewhat rough with stipitate glands.

*Sepal shape*.—Apex: Cirrhose. Base: Flat at union with receptacle.

*Sepal margin*.—Margins have weak foliaceous appendages on three of the five sepals.

*Sepal size*.—Typically 20 mm long by 6 mm wide.

*Receptacle*.—Texture: Smooth. Size: 6 mm in height by 6 mm wide. Color: Green Group 138B with weak pigments the color of Greyed-Purple Group 183A. Shape: Campanulate.

*Pedicel*.—Surface: Somewhat rough with many stipitate glands. Length: 25 to 30 mm. Diameter: 2 mm on average. Color: Yellow-Green Group 145A. Anthocyanic pigments the color of Greyed-Orange Group 176A observed. Strength: Moderate.

*Peduncle*.—Length: 25 to 60 cm. Texture: Large prickles. Diameter: 2 to 3 mm. Color: Yellow-Green Group 146D with Greyed-Orange Group 176A.

Flower bud development: Flower buds are borne in clusters of 5 to 15 flower buds per stem, resembling a panicle.

Flower bloom:

*Fragrance*.—Moderate floral scent.

*Duration*.—The blooms have a duration on the plant of approximately 15 days. Petals fall cleanly away from plant after flowers have fully matured.

*Size*.—Flower diameter is 80 to 90 mm when open. Flower depth is 30 mm.

*Flower shape*.—General shape is an open cup double flower, with petals that curve out from the center.

*Shape of flower, side view*.—Upon opening the upper portion is flat. The lower portion is concave.

Petalage: Under normal conditions, flowers have 65 petals total, 10 of which are petaloids.

General tonality of flower: Open flowers are Red-Purple Group 58C. After 7 to 10 days, tonality changes to Red-Purple Group 62B.

Petal color:

*Upon opening, outer petals*.—Upper surface: Red-Purple Group 58C. Lower surface: Red-Purple Group 58D with intonations of Red-Purple Group N66C at margins. Some petals are splashed with Green-White Group 157A.

*Upon opening, inner petals*.—Upper surface: Red Group 55A to 55B. Lower surface: Red-Purple Group 58D.

*Basal petal spots, upon opening*.—Upper surface: Yellow Group 4C. Lower surface: Yellow Group 4C.

*After opening, outer petals and inner petals*.—Upper surface: Red-Purple Group 65A splashed with Red-Purple Group 62D at the petal base. Lower surface: Red-Purple Group 63B to 63C.

*Basal petal spots, after opening*.—Upper surface: Green-White Group 157A. Lower surface: Green-White Group 157A.

Petals:

*Petal reflex*.—Somewhat reflexed.

*Margin*.—Entire and uniform. Weak undulations of margin observed.

*Shape*.—Generally narrow elliptic. Apex shape: Rounded. Base shape: Acute.

*Size*.—40 mm (l)×40 mm (w).

*Texture*.—Smooth.

*Thickness*.—Average.

Petaloids:

*Size*.—15 mm (l) by 8 mm (w).

*Quantity*.—10 on average.

*Shape*.—Elliptic, with acute base and apex.

*Color*.—Red Group 55A on upper surface. Red Group 55B on lower surface.

Reproductive organs:

*Pollen*.—None observed.

*Anthers*.—Size: 2 mm in length. Color: Yellow Group 11B. Quantity: 55 on average.

*Filaments*.—Color: Yellow Group 13B. Length: 5 mm.

*Pistils*.—Length: 4 mm. Quantity: 35 on average.

*Stigmas*.—Color: Green-White Group 157A.

*Styles*.—Color: Green-White Group 157A.

*Location of stigmas*.—Inferior in location relative to the length of the filaments and the height of the anthers.

*Hips*.—None Observed.

PLANT

Plant growth: Upright, bushy. Plants are 40 cm in height, and 40 cm wide.

Stems:

*Color*.—Juvenile growth: Yellow-Green Group 146D with light intonations of Greyed-Red Group 178B. Mature growth: Yellow-Green Group 146B.

*Length*.—On average, canes are 20 cm from the base of the plant to the flowering portion.

*Diameter*.—5 mm.

*Internodes*.—On mature canes, there is an average distance of 30 mm between nodes.

*Surface texture*.—Young wood: Smooth. Older wood: Smooth.

Long prickles:

*Incidence*.—7 prickles per 10 cm of stem.

*Size*.—Average length of prickles on mature stems is 6 mm.

*Shape*.—Upper portion is linear. Lower portion is concave.

*Color*.—Juvenile prickles: Greyed-Red Group 182A. Mature prickles: Greyed-Orange Group 166D.

Plant foliage:

*Compound leaf*.—120 mm (l)×75 (w).

*Quantity*.—3 leaves per 10 cm of stem on average.

*Leaf bearing angle to the stem*.—45 degrees.

*Color of juvenile foliage*.—Upper side: Yellow-Green Group 146C. Margins are Greyed-Orange Group 176A. Lower side: Yellow-Green Group 146C.

*Color of mature foliage*.—Upper side: Yellow-Green Group 147A. Lower side: Yellow-Green Group 147C.

Plant leaves and leaflets:

*Stipules*.—Size: 5 mm in length. About 2 mm wide. Quantity: 2 per compound leaf. Shape: Linear, slightly broad based with outward extending apices. Margins: Finely serrated with few stipitate glands. Color: Yellow-Green Group 147A. Petiole: Length:

12 mm. Diameter: 2 mm. Upper surface: Color: Yellow-Green Group 144B with Greyed-Purple Group 185A. Lower surface: Color: Yellow-Green Group 144D. Rachis: Length: 35 to 45 mm. Upper surface: Color: Yellow-Green Group 144B with Greyed-Purple Group 185A. Lower surface: Color: Yellow-Green Group 144D. Leaflet: Quantity: Normal number of leaflets per leaf in the middle of the stem is 7 leaflets. Margins: Serrated. Size: Average size of the terminal leaflet on normal leaves is 45 mm in length by 30 mm wide. Shape: Generally elliptical. Base: Rounded. Apex: Acute. Cuspidate. Texture: Smooth. Thickness: Average. Arrangement: Odd pinnate. Venation: Reticulate. Glossiness: Moderately glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Compact Floribunda rose class named 'Poulpal036', substantially as illustrated and described herein, due to its abundant pink flowers, disease resistance, and extended period of bloom.

* * * * *

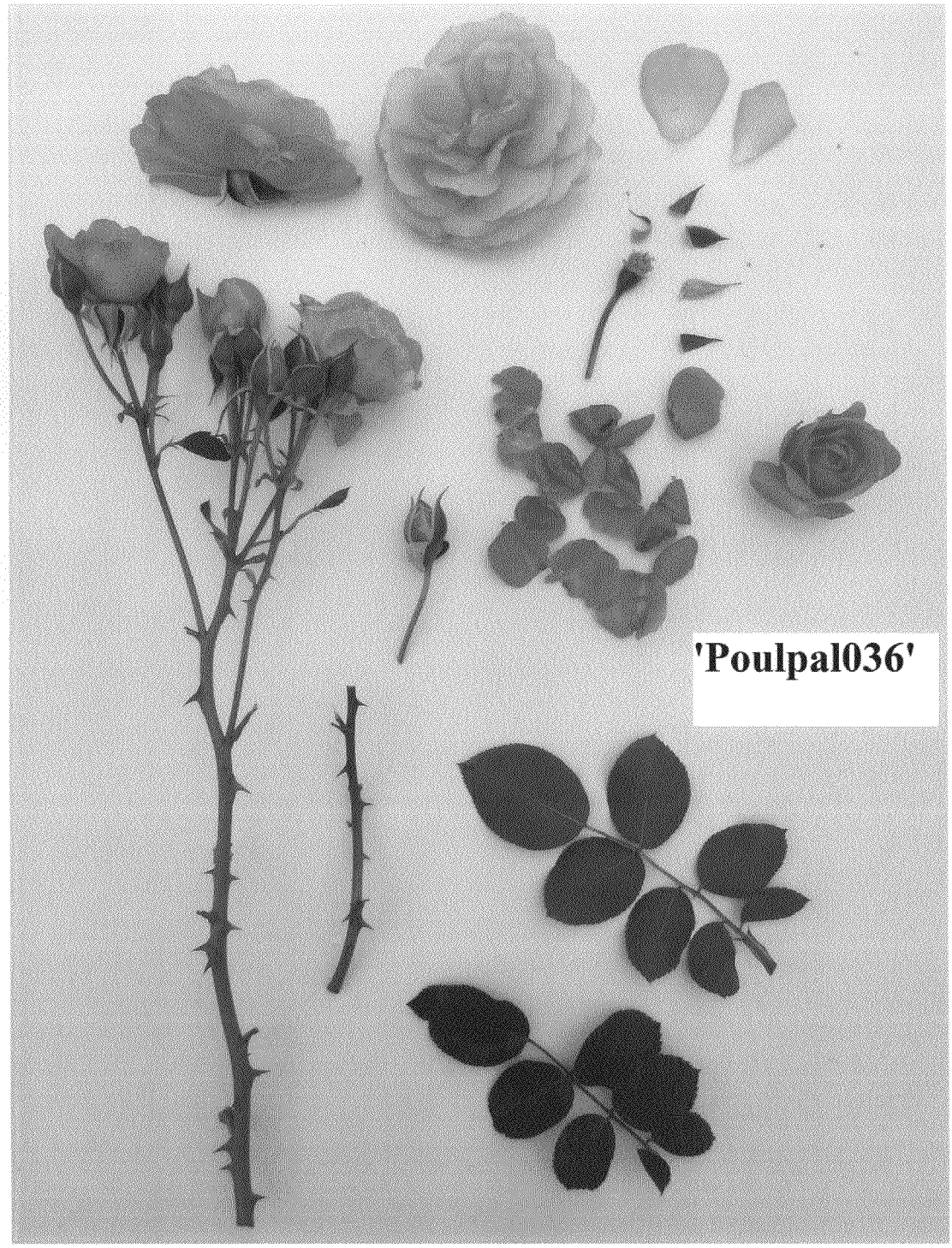
'Poulpal036'